(12) United States Patent
Bakos et al.

(10) Patent No.: US 7,967,741 B2
(45) Date of Patent: Jun. 28, 2011

(54) ENDOSCOPIC GUIDE DEVICE

(75) Inventors: Gregory J. Bakos, Mason, OH (US);
Christie M. Cunningham, Cincinnati, OH (US); David Stefanchik, Morrow, OH (US); James W. Voegele, Cincinnati, OH (US); Michael J. Stokes, Cincinnati, OH (US); Christopher J. Hess, Cincinnati, OH (US); James T. Spivey, Cincinnati, OH (US); Gary L. Long, Cincinnati, OH (US); Kurt R. Bally, Lebanon, OH (US); Ragae M. Ghabrial, Cincinnati, OH (US); Rudolph H. Nobis, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1056 days.

(21) Appl. No.: 11/742,948

(22) Filed: May 1, 2007

(65) Prior Publication Data

US 2008/0275297 A1    Nov. 6, 2008

(51) Int. Cl.
*A61B 1/00*    (2006.01)
*A61F 2/00*    (2006.01)
*A61F 13/00*   (2006.01)
*A61M 5/32*    (2006.01)

(52) U.S. Cl. .......... 600/102; 600/37; 600/104; 604/175
(58) Field of Classification Search ............. 600/102, 600/127, 129, 37; 604/175; 606/233
See application file for complete search history.

(56) References Cited

U.S. PATENT DOCUMENTS

| 3,557,780 | A |   | 1/1971 | Sato et al. |
| 4,108,211 | A |   | 8/1978 | Tanaka et al. |
| 4,290,421 | A |   | 9/1981 | Siegmund |
| 4,593,681 | A |   | 6/1986 | Soni |
| 4,633,865 | A |   | 1/1987 | Hengstberger et al. |
| 4,686,965 | A |   | 8/1987 | Bonnet et al. |
| 4,759,348 | A |   | 7/1988 | Cawood |
| 4,762,519 | A | * | 8/1988 | Frimberger ............. 604/164.01 |
| 4,794,912 | A |   | 1/1989 | Lia |
| 4,826,481 | A | * | 5/1989 | Sacks et al. .................. 604/516 |
| 4,941,454 | A |   | 7/1990 | Wood et al. |
| 4,962,751 | A |   | 10/1990 | Krauter |
| 4,972,827 | A |   | 11/1990 | Kishi et al. |
| 5,014,515 | A |   | 5/1991 | Krauter |
| 5,025,778 | A |   | 6/1991 | Silverstein et al. |

(Continued)

FOREIGN PATENT DOCUMENTS

JP    5115423 A    5/1993

*Primary Examiner* — Linda C Dvorak
*Assistant Examiner* — Alireza Nia
(74) *Attorney, Agent, or Firm* — Nutter McClennen & Fish LLP (57) ABSTRACT

Various exemplary methods and devices are provided for manipulating and/or anchoring devices and body parts during surgical procedures. In one embodiment, an anchor member is provided for anchoring a device or body part to tissue, such as an internal wall of a body cavity. The device can be, for example, an endoscopic device, an accessory channel coupled to an endoscopic device, or a support member adapted to support or manipulate an organ. The anchor member can include or form an opening through which the device can be inserted. The anchor member or device can thus be manipulated relative to the tissue to control movement of and/or provide support to the device, tools inserted through the device, and/or organs grasped by the device or tools.

14 Claims, 7 Drawing Sheets

U.S. PATENT DOCUMENTS

| | | |
|---|---|---|
| 5,167,627 A | 12/1992 | Clegg et al. |
| 5,184,601 A | 2/1993 | Putman |
| 5,297,536 A | 3/1994 | Wilk |
| 5,299,562 A | 4/1994 | Heckele et al. |
| 5,331,948 A | 7/1994 | Utsumi et al. |
| 5,337,732 A | 8/1994 | Grundfest et al. |
| 5,351,676 A | 10/1994 | Putman |
| 5,360,429 A | 11/1994 | Jeanson et al. |
| 5,375,588 A | 12/1994 | Yoon |
| 5,425,732 A | 6/1995 | Ulrich et al. |
| 5,429,598 A | 7/1995 | Waxman et al. |
| 5,437,669 A | 8/1995 | Yuan et al. |
| 5,470,337 A * | 11/1995 | Moss .......................... 606/139 |
| 5,540,648 A | 7/1996 | Yoon |
| 5,755,796 A | 5/1998 | Ibo et al. |
| 5,813,976 A * | 9/1998 | Filipi et al. .................... 600/102 |
| 5,928,233 A | 7/1999 | Apfelbaum et al. |
| 6,019,760 A | 2/2000 | Metz-Stavenhagen et al. |
| 6,535,764 B2 * | 3/2003 | Imran et al. .................... 607/40 |
| 7,169,104 B2 * | 1/2007 | Ueda et al. .................... 600/104 |
| 7,744,613 B2 * | 6/2010 | Ewers et al. .................. 606/153 |
| 2003/0130669 A1 * | 7/2003 | Damarati ...................... 606/151 |
| 2005/0171610 A1 | 8/2005 | Humphreys et al. |
| 2005/0228381 A1 | 10/2005 | Kirschman |
| 2005/0228501 A1 | 10/2005 | Miller et al. |
| 2005/0240265 A1 | 10/2005 | Kuiper et al. |
| 2006/0241771 A1 | 10/2006 | Gordon et al. |
| 2006/0247673 A1 | 11/2006 | Voegele et al. |
| 2006/0265074 A1 | 11/2006 | Krishna et al. |
| 2007/0135678 A1 * | 6/2007 | Suzuki ........................... 600/37 |

\* cited by examiner

ENDOSCOPIC GUIDE DEVICE

BACKGROUND

The popularity of minimally invasive surgical procedures is increasing as it allows for smaller incisions which tend to reduce recovery time and complications during surgical procedures. One option that is being widely used in a wide range of procedures is endoscopic devices, which are one of the least invasive surgical methods used today as access to a surgical site can be provided through a natural body orifice or a small incision. Endoscopes are used often in a variety of peritoneal surgeries that need access to the peritoneal cavity, including appendectomies and cholecystectomies.

During procedures that utilize endoscopic devices, there is often a need to manipulate and position the device and organs to facilitate stabilization of the devices and the organs during surgical procedures. This presents challenges as the distal end of the endoscope is often located inside the body far from the proximal end at which movement of the device is controlled. Further complications involve the consistency of the organs, which can often be large and relatively dense, making surgical procedures difficult to perform without being able to manipulate and stabilize the organs.

Accordingly, there is a need for improved methods and devices for anchoring endoscopic devices and for manipulating body parts during surgical procedures.

SUMMARY

The present invention provides various methods and devices for anchoring endoscopic devices and/or manipulating objects such as a body organ. In one embodiment, the method can include endoscopically implanting an anchor member in an internal wall of a body cavity such that the anchor member defines an opening, and inserting a device through the opening in the anchor member to anchor a distal portion of the device to the wall of the body cavity. The device can be, for example, an endoscope or an accessory channel slidably coupled to an endoscope. The method can further include engaging a body organ with a distal end of the device, and sliding the device relative to the anchor member to reposition the body organ.

In one embodiment, the anchor member can be inserted through an endoscope to endoscopically implant the anchor member, and the anchor member can be manipulated to engage the internal wall of the body cavity. A grasping device can be disposed through the endoscope and used to manipulate the anchor member. In one exemplary embodiment, the anchor member includes a first terminal end that is implanted at a first anchor site on the internal wall of the body cavity, and a second terminal end that is implanted at a second anchor site on the internal wall of the body cavity. The anchor member can extend between the first and second anchor sites such that the opening is formed between the anchor member and the internal wall of the body cavity.

The anchor member can have a variety of other configurations. For example, the anchor member can include a hoop defining the opening and having first and second tissue-penetrating legs extending therefrom for engaging the wall of the body cavity. In another embodiment, the anchor member can include an elongate rod having first and second tissue-penetrating legs located on opposed terminal ends thereof for engaging the wall of the body cavity. In yet another embodiment, the anchor member can include a suture having first and second tissue-engaging members coupled to opposed terminal ends thereof for engaging the internal wall of the body cavity. The opening is formed between the suture and the internal wall of the body cavity when the first and second tissue-engaging members are implanted in the internal wall of the body cavity. The first and second tissue-engaging members can be passed through the internal wall of the body cavity to the external surface of the body, and the first and second tissue-engaging members can be manipulated to pull the device against the internal wall of the body cavity.

The present invention also provides methods for manipulating a body part during a surgical procedure. In one embodiment, the method can include implanting an anchor member in an internal wall of a body cavity, inserting a support member through an endoscope, and coupling a distal portion of the support member to the anchor member. The method further includes grasping a body part with a distal end of the support member, and sliding the support member relative to the anchor member to manipulate the body part by, for example, applying tension to a proximal end of the support member.

The anchor member can be implanted in a number of ways. In one embodiment, the anchor member can be implanted by inserting the anchor member through an endoscope, and implanting at least one tissue-engaging member formed on the anchor member in the internal wall of the body cavity. In order to implant the at least one tissue-engaging member, a first tissue-engaging member formed on a first terminal end of the anchor member can be implanted at a first anchor site on the internal wall of the body cavity, and a second tissue-engaging member formed on a second terminal end of the anchor member can be implanted at a second anchor site on the internal wall of the body cavity such that the anchor member extends between the first and second anchor sites. An opening is formed between the anchor member and the internal wall of the body cavity. A distal portion of the support member can be coupled to the anchor member by inserting the support member through the opening. In another embodiment, the anchor member can be implanted by inserting the anchor member through an external surface of the body to position a distal portion of the anchor member within the body cavity. The anchor member can include a cannula that is inserted through the external surface of the body, and a loop that extends from the cannula and is positioned within the body cavity. A distal portion of the support member can be coupled to the anchor member by inserting the support member through the loop.

Methods are also provided for supporting an endoscopic device. In one embodiment, the method can include implanting an anchor member in an internal wall of the body cavity, inserting an endoscope through a body lumen to position a distal portion of the endoscope adjacent to the anchor member, and coupling an accessory channel removably coupled to the endoscope to the anchor member such that the accessory channel is anchored to the body cavity and supported related to the endoscope. In one exemplary embodiment, the method can further include applying tension to the anchor member to maintain the accessory channel in a fixed position relative to the body cavity, and inserting a device through the accessory channel such that a distal end of the device extends distally from a distal end of the accessory channel.

The anchor member can have a variety of configurations, and can include, for example, a hoop formed thereon. Coupling the accessory channel to the anchor member can include inserting the accessory channel through the hoop. In another embodiment, the anchor member can include opposed terminal ends that are anchored to the body cavity such that an opening extends between the anchor member and the body cavity. Coupling the accessory channel to the anchor member can include inserting the accessory channel through the opening.

The present invention further provides methods for supporting an organ during a surgical procedure. The method can include inserting an elastic member through an endoscope, and implanting a first anchoring element formed on a first end of the elastic member in a body part. Tension can be applied to a second end of the elastic member to reposition the body part, and a second anchoring element formed on the second end of the elastic member can be implanted in tissue located a distance away from the body part to maintain the body part in a substantially fixed position.

BRIEF DESCRIPTION OF THE DRAWINGS

The invention will be more fully understood from the following detailed description taken in conjunction with the accompanying drawings, in which.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary methods and devices are provided for manipulating and/or anchoring devices and body parts during surgical procedures. In general, an anchor member is provided for anchoring a device or body part to tissue, such as an internal wall of a body cavity. The device can be, for example, an endoscopic device, an accessory channel coupled to an endoscopic device, or a support member adapted to support or manipulate an organ. The anchor member can include or form an opening through which the device can be inserted. The anchor member or device can thus be manipulated relative to the tissue to control movement of and/or provide support to the device, tools inserted through the device, and/or organs grasped by the device or tools.

Figure 1:
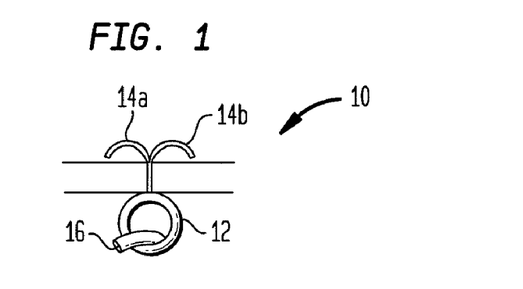
FIG. 1 is a side view of one embodiment of an anchor member having a hoop for receiving a device therethrough, shown implanted in tissue.

FIGS. 1-5 illustrate various exemplary embodiments of an anchor member for implantation into tissue, e.g., an internal wall of a body cavity. FIG. 1 illustrates one exemplary embodiment of an anchor member 10 that generally includes a hoop 12 with first and second tissue-penetrating legs 14a, 14b extending from the hoop 12. The hoop 12 can have any shape and size, but it is preferably adapted to receive a device such as a support member, an endoscopic device, an accessory channel coupled to an endoscopic device, etc. As shown in FIG. 1, the hoop 12 defines an opening 16 therethrough for receiving a device. The first and second tissue-penetrating legs 14a, 14b can also have a variety of configurations, but they are preferably adapted to be inserted through a wall of a body cavity to anchor the hoop 12 to the wall. A person skilled in the art will appreciate that, while described in relation to a wall of a body cavity, the anchor member 10 can be inserted through and anchored to any tissue in the body. In the illustrated embodiment shown in FIG. 1, the terminal ends of the tissue-penetrating legs 14a, 14b are generally elongate components that can have a straight configuration for enabling penetration into tissue, and that can be bent over after they penetrate tissue to secure them to the external wall of the body cavity. A person skilled in the art will also appreciate that the first and second tissue-penetrating legs can be secured to tissue using a variety of other techniques, either before or after the tissue-penetrating legs 14a, 14b are bent, including the use of sutures or a surgical adhesive. One skilled in the art will appreciate that the first and second tissue-penetrating legs 14a, 14b can be made from a variety of biocompatible materials that have properties sufficient to enable the first and second tissue-penetrating legs 14a, 14b to be inserted and penetrated through the wall of a body cavity. The material can also be a bioabsorbable material with a strength profile that is adapted for the procedure and holding time needed. The anchor may also have a feature, such as a reduced diameter or thinned region, that enables the suture material to separate and be released from the anchor.

Figure 2:
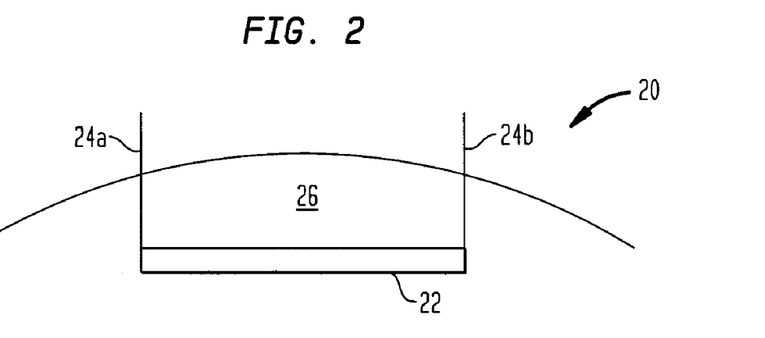
FIG. 2 is a side view of another embodiment of an anchor member having an elongate rod forming an opening for receiving a device therethrough, shown implanted in tissue.

FIG. 2 illustrates another exemplary embodiment of an anchor member 20 that generally includes an elongate rod 22 with first and second tissue-penetrating legs 24a, 24b located on opposed terminal ends of the elongate rod 22. The first and second tissue-penetrating legs 24a, 24b preferably have a length that allows the legs 24a, 24b to be anchored to tissue such that the elongate rod 22 is spaced a distance apart from the tissue surface. As a result, an opening 26 is defined between the elongate rod 22 and the tissue surface for receiving various devices therethrough. The first and second tissue-penetrating legs 24a, 24b can be adapted to be penetrated through a wall of a body cavity, and they can be secured to an external wall of the body cavity using a variety of techniques, for example, using sutures coupled to the tissue penetrating legs 24a, 24b that can be knotted or tied to secure them to an external surface of the body. Alternatively, the first and second tissue-penetrating legs 24a, 24b can be replaced with sutures for securing the rod 22 to tissue. The rod can also have a variety of configurations, and it can be rigid, flexible, or deformable, and/or it can have features such as holes, raised surface features, or a combination thereof to ease or fixate attachment of a suture thereto.

Figure 3:
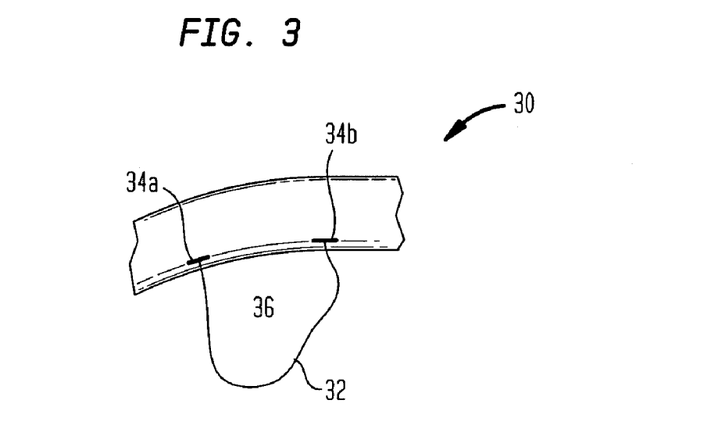
FIG. 3 is a side view of yet another embodiment of an anchor member having a suture with first and second tissue-engaging members implanted in tissue.

FIG. 3 illustrates yet another exemplary embodiment of an anchor member 30 that generally includes a suture 32 having first and second tissue-engaging members 34a, 34b coupled to opposed terminal ends of the suture 32. The first and second tissue-engaging members 34a, 34b can have a variety of configurations. For example, the first and second tissue-engaging members 34a, 34b can be in the form of t-bars or staples that are adapted to engage tissue, as shown. A person skilled in the art will appreciate that any component can be used as the first and second tissue-engaging members 34a, 34b to anchor the suture 32 to an internal wall of a body cavity. Once anchored, an opening 36 is formed between the suture 32 and the internal wall of the body cavity for receiving various devices. A person skilled in the art will appreciate that the suture 32 can have any length in order to form an opening 36 with a size that is sufficient for a device to pass therethrough.

Figure 4:
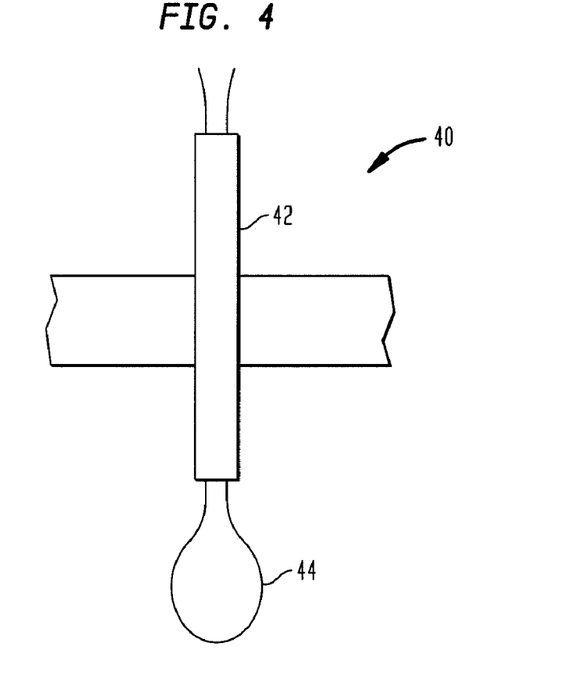
FIG. 4 is a side view of another embodiment of an anchor member having a cannula inserted through a body cavity and a loop extending into the body cavity.

FIG. 4 illustrates another exemplary embodiment of an anchor member 40 that generally includes a cannula 42 having a loop 44 extending therefrom for extending into a body cavity. The cannula 42 can be used to insert the anchor member 40 through tissue and into a body cavity. For example, a trocar or other device can be used to insert the cannula 42 through tissue and into the body cavity such that the cannula 42 forms a working channel extending into the body cavity. The loop 44 can extend from the distal end of the cannula 42 and it can be adapted to receive an endoscope or support member therethrough. A person skilled in the art will appreciate that the loop 44 can have any size or shape that forms an opening that is sufficient for a device to pass therethrough. The loop 44 can also be permanently fixed to the cannula 42 or it can be a separate component that is passed through an inner lumen of the cannula 42 after the cannula 42 has been inserted into the body cavity. Further, the loop 44 can be movable within the inner lumen of the cannula 42 by advancing and retracting the loop 44 relative to the cannula 42.

Figure 5:
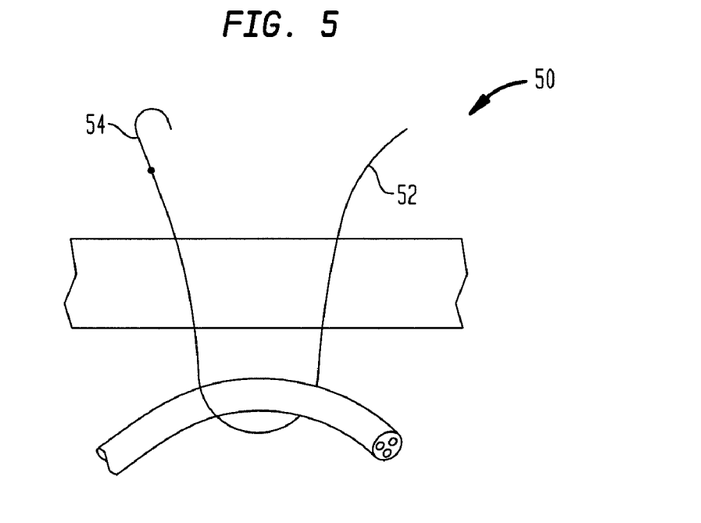
FIG. 5 is a side view of another embodiment of an anchor member having a suture or wire attached to a hook for puncturing through a body cavity, shown implanted in tissue.

FIG. 5 illustrates another exemplary embodiment of an anchor member 50 that generally includes a length of suture or wire 52 having a tissue-penetrating member 54 disposed on a terminal end thereof. While the suture or wire 52 can have any configuration, in one embodiment it can be rigid enough to allow insertion of the suture or wire 52 through the external surface of the body and into a body cavity, but flexible enough to allow the suture or wire 52 to be manipulated once inside the body cavity. The tissue-penetrating member 54 can be adapted to facilitate penetration through the tissue. For example, the penetrating member can be in the form of a hook as shown. The hook can have any size or shape to facilitate penetrating and retrieval through the target tissue(s) or organ. In use, the tissue-penetrating member 54 can be inserted through an external wall of the body cavity at a first anchor site. The tissue-penetrating member can then be inserted through a second anchor site located on the internal wall of the body cavity. A portion of the suture or wire 52 can remain between the first and second anchor sites to form an opening between the suture or wire 52 and the tissue surface with a size that is sufficient for a device to pass through. For example, the newly created loop could be adapted to receive an endoscopic device, as shown, which could be repositionable by manipulating the suture or wire attached thereto.

A person skilled in the art will appreciate that the anchor members shown in FIGS. 1-5 are merely exemplary and that the anchor member can have a variety of configurations to allow the anchor member to be attached to tissue and to form an opening for receiving various devices.

Figure 6A:
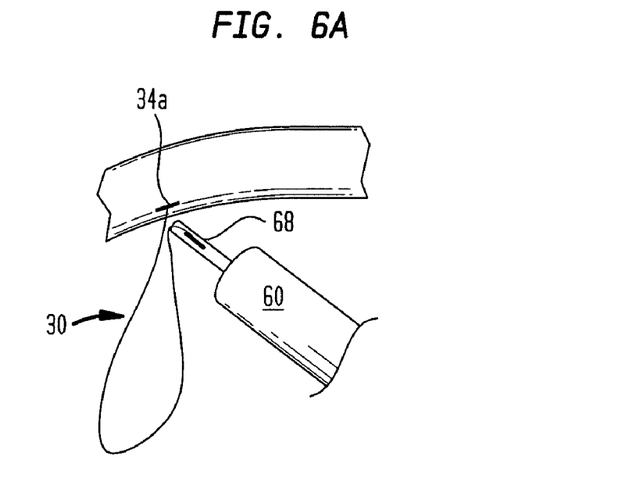
FIG. 6A is a side view of a first tissue-engaging member of an anchor member being delivered endoscopically and implanted in an internal wall of a body cavity.
Figure 6B:
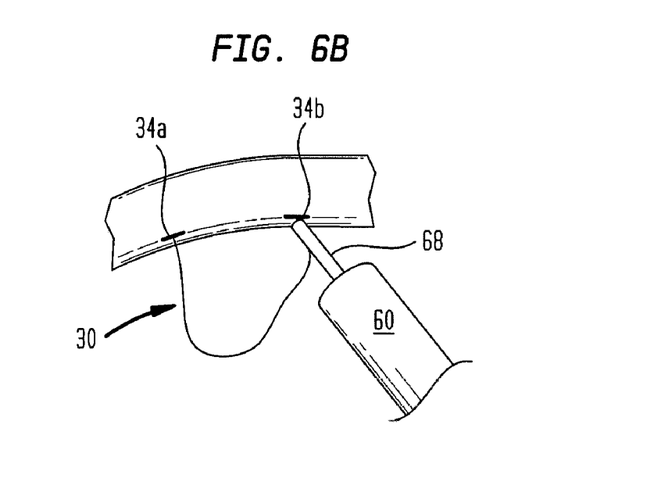
FIG. 6B is a side view of a second tissue-engaging member of the anchor member shown in FIG. 6A being implanted in an internal wall of a body cavity.

The present invention also provides methods for endoscopically implanting an anchor member in an internal wall of a body cavity. Certain anchor members described above are particularly suited for endoscopic implantation, including the anchor members 10, 20, 30 shown in FIGS. 1-3. In one exemplary embodiment, shown in FIGS. 6A-B, an endoscope 60 can be inserted translumenally, e.g., through a natural orifice, and positioned adjacent to tissue in a body cavity to which an anchor member, e.g. anchor member 30 of FIG. 3, will be implanted. The anchor member 30 can be inserted through an inner lumen of the endoscope 60 to extend from the distal end of the endoscope 61. A variety of techniques can be used to manipulate the anchor member 30 and to implant the anchor member 30 in the internal wall of the body cavity. In one embodiment, a grasping device 68 can be inserted through the inner lumen of the endoscope 60 and it can used to manipulate the anchor member 30 and implant the anchor member 30 in the internal wall of the body cavity. FIG. 6 illustrates the first and second tissue-engaging members 34a, 34b of anchor member 30 being implanted in tissue. In particular, a distal end of the grasping device 68 can grab the first tissue-engaging member 34a and it can be manipulated to implant the first tissue-engaging member 34a into a first anchor site in the internal wall of the body cavity, as shown in FIG. 6A. The grasping device 68 can similarly be manipulated to implant the second tissue-engaging member 34b into a second anchor site in the internal wall of the body cavity, as shown in FIG. 6B. After implantation of the anchor member 30, the grasping device 68 can be removed from the endoscope 60, and the anchor member can be used to anchor a device, such as the distal end of the endoscope 60, or to manipulate an organ, as will be discussed in more detail below. While FIG. 6 illustrates the anchor member 30 of FIG. 3 being implanted endoscopically, the anchor members 10, 20 of FIGS. 1 and 2 can also be implanted endoscopically in an internal wall of a body cavity. Further, a person skilled in the art will appreciate that any anchor member can be implanted endoscopically with the method described above. Moreover, a person skilled in the art will also appreciate that any of the anchor members described above can also be implanted through an external surface of the body and used with any of the methods described herein.

Figure 7:
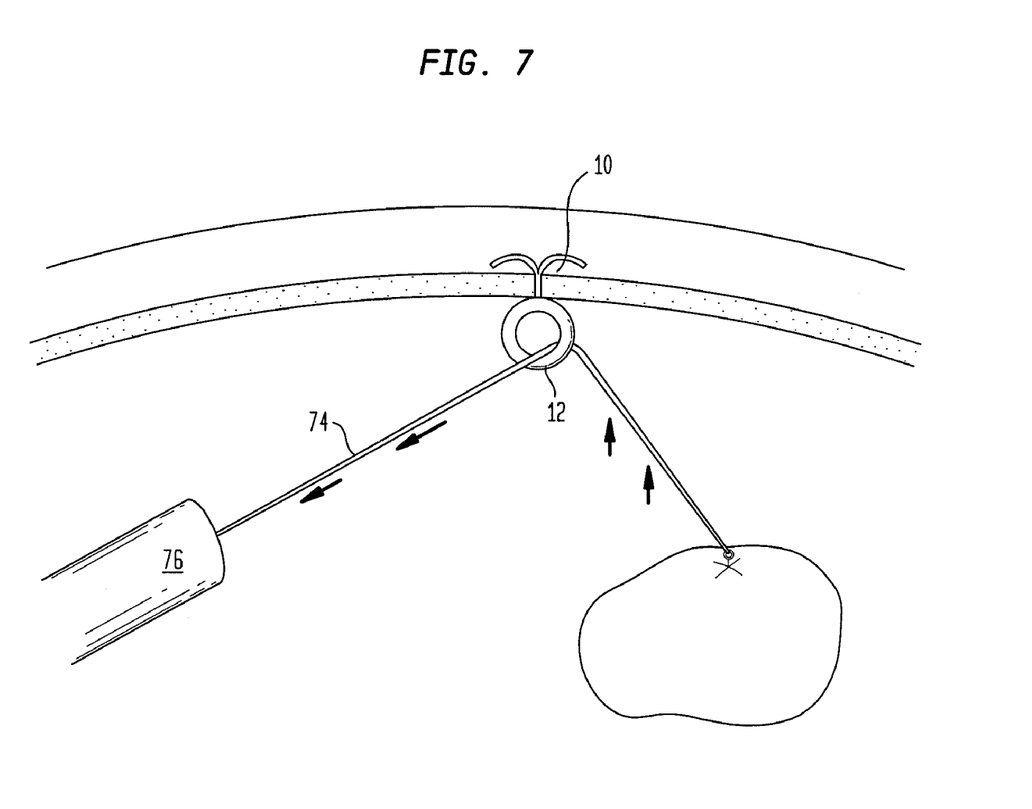
FIG. 7 is a side view of an anchor member implanted in tissue and have a support member extending therethrough and coupled to a body part for manipulating the body part.

The present invention also provides methods for manipulating an organ during a surgical procedure. In one exemplary embodiment, shown in FIG. 7, an endoscope 76 can be inserted translumenally, e.g., through a natural orifice, and positioned adjacent to tissue in a body cavity to which an anchor member has been implanted. FIG. 7 illustrates the anchor member 10 of FIG. 1, however any anchor member can be used. A support member 74 adapted to manipulate an organ can be disposed through the endoscope 76 and a distal end of the support member 74 can be coupled to the anchor member 10. For example, as shown in FIG. 7, the distal end of the support member 74 is inserted through a hoop 12 of the anchor member 10. Once passed through the hoop 12, the distal end of the support member 74 can be coupled to an organ to be manipulated. Sutures, staples, hooks, or various other techniques can be used to engage the organ. In the illustrated embodiment, the support member 74 is coupled to the organ by suturing the distal end of the support member 74 to the organ. A tool inserted through the endoscope 76 can be used to manipulate the support member 74 and anchor it to tissue. Once the support member 74 is mated to the organ, the support member 74 can be slid or otherwise moved relative to the anchor member 10, for example, by applying tension to a proximal end of the support member 74, to thereby move the organ. The proximal end can optionally be maintained at a fixed position, e.g., by tying to a table, to hold the organ in a desired position during a surgical procedure.

Figure 8A:
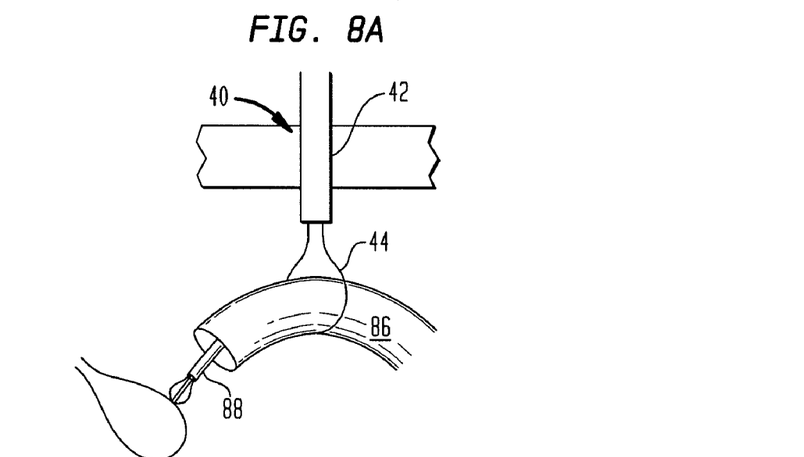
FIG. 8A is a side view of an anchor member inserted through tissue and having an endoscope disposed therethrough with a grasping element extending from the endoscope for manipulating a body part.
Figure 8B:
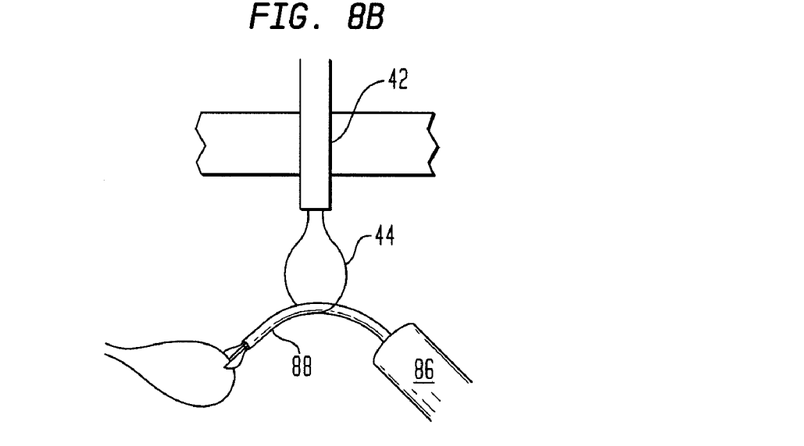
FIG. 8B is a side view of the anchor member shown in FIG. 8A having the grasping element disposed therethrough.
Figure 8C:
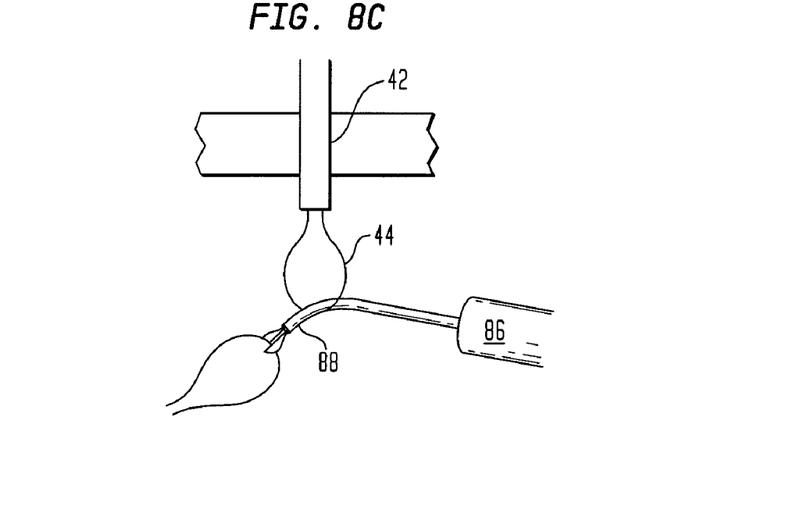
FIG. 8C is a side view of the anchor member shown in FIG. 8A having the grasping element disposed therethrough with the grasping element being moved relative to the anchor member to manipulate the body part.

Methods are also provided for anchoring a device, such as an endoscope or an accessory channel coupled to an endoscope, to tissue. FIGS. 8A-8C illustrate the anchor member 40 of FIG. 4 implanted in a body cavity. As shown in FIG. 8A, an endoscope 86 can be positioned through the loop 44 of the anchor member 40. A portion of the loop 44 that extends proximally from the cannula 42 and remains external to the body can be pulled to tighten the loop 44 and anchor the endoscope 86 to the internal wall of the body cavity to provide support for steering the endoscope 86 in the body cavity. Alternatively, or in addition, a device, such as a grasping device 88, can be passed through the endoscope 86 and used, for example, to grasp an organ or body part to manipulate a body part. The endoscope 86 can optionally be moved proximally, as shown in FIG. 8B, leaving the grasping device 88 positioned within the loop 44 of the anchor member 40. The grasping device 88 can thus be moved relative to the anchor member 40, as shown in FIG. 8C, to move and manipulate the body part. A person skilled in the art will appreciate that any device can be passed through the endoscope and used for a variety of functions, and that the anchor member 40 can be used to anchor the endoscope and/or any device inserted through the endoscope.

Figure 9A:
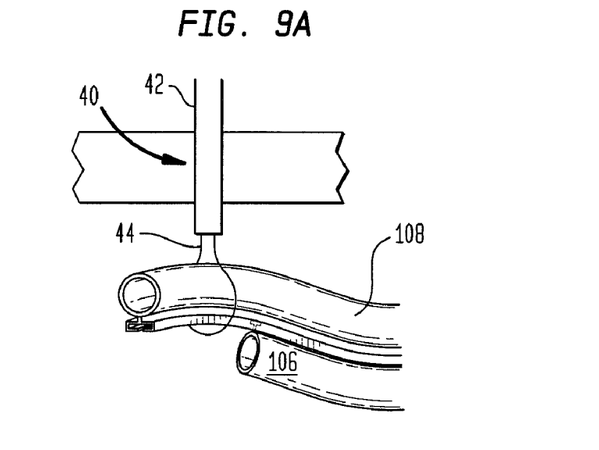
FIG. 9A is a perspective view of an anchor member inserted through tissue and having an accessory channel on an endoscope disposed therethrough.
Figure 9B:
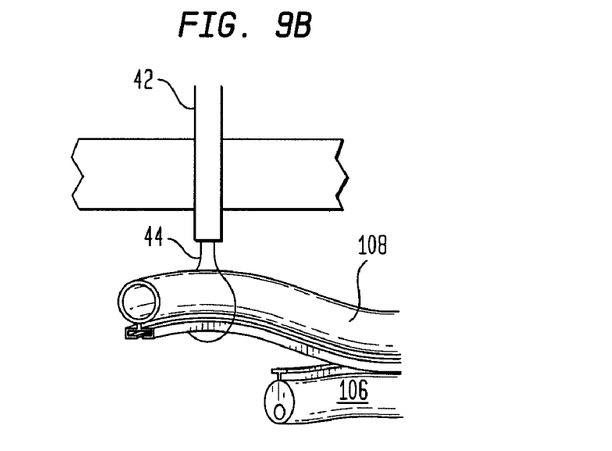
FIG. 9B is a perspective view of the anchor member FIG. 9A and having the accessory channel disposed therethrough and separate from the endoscope.
Figure 9C:
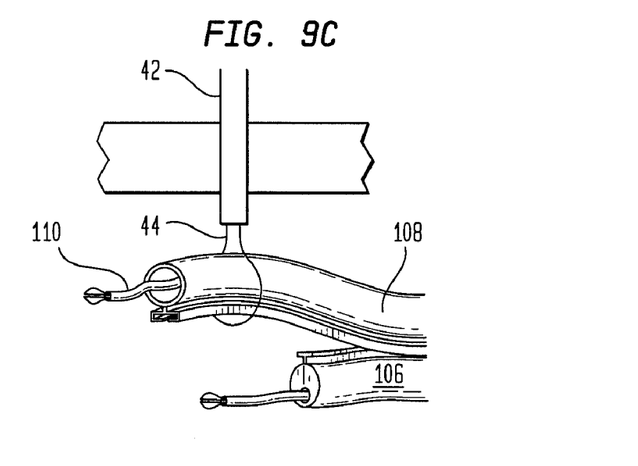
FIG. 9C is a perspective view of the anchor member of FIG. 9A and having the accessory channel disposed therethrough with a grasping element extending from the accessory channel and the endoscope for manipulating a body part.

In another embodiment, an accessory channel 108 on an endoscope 106 can be anchored to tissue, as shown in FIGS. 9A-9C. The endoscope 106 can be positioned proximate to the loop 44 of the anchor member 40, and the accessory channel 108 can be positioned through the loop 44, as shown in FIG. 9A. The accessory channel 108 can be separated from the endoscope 106, as shown in FIG. 9B, to allow the endoscope 106 to be positioned a distance apart from the accessory channel 108. The loop 44 can be pulled to tighten the loop 44, anchoring the accessory channel 108 to the internal wall of the body cavity to provide support for the accessory channel 108 when additional devices are passed therethrough. The endoscope 106 can be used to view the devices passed through the accessory channel 108. Additional devices can also be passed through the endoscope 106, as shown in FIG. 9C. For example, a grasping device 110 can be passed through the accessory channel 108 and the endoscope 106 to grasp and manipulate tissue or body parts.

Figure 10:
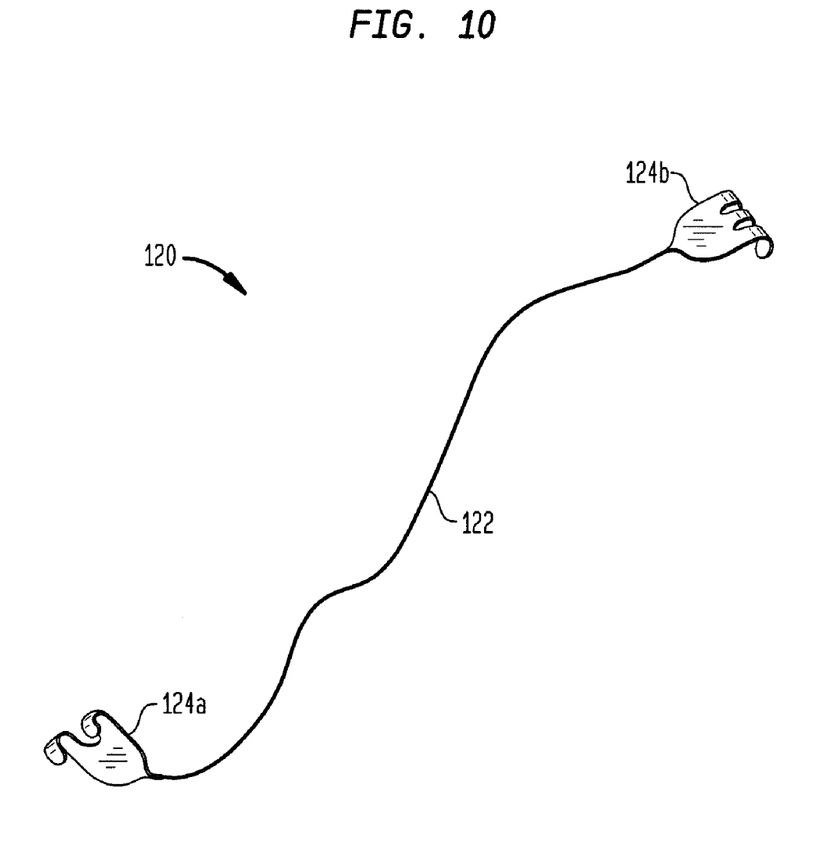
FIG. 10 is a perspective view of another embodiment of an anchor member having a length of elastic material with first and second tissue grasping members disposed thereon for manipulating an organ.

FIG. 10 illustrates another embodiment of a technique for manipulating a body part. In this embodiment, an anchor member 120 has an elastic member 122 with first and second tissue grasping members 124a, 124b disposed on terminal ends thereof. The tissue grasping members 124a, 124b can have a variety of configurations for grasping tissue or body parts. In the illustrated embodiment, the tissue grasping members 124a, 124b are in the form of hooks with several teeth for penetrating into tissue. The first tissue grasping member 124a can be coupled to the body part to be manipulated, and tension can be applied to the elastic member 122 to position the body part as desired, for example, during a surgical procedure. The second tissue grasping member 124b can then be anchored at a variety of locations within the body, for example, a wall of a body cavity, to maintain the tension of the elastic member 122 and the position of the body part.

A person skilled in the art will appreciate that any of the methods described above can be achieved using various anchoring devices.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical method, comprising:
    introducing an anchor member endoscopically through a natural orifice;
    implanting the anchor member directly in an internal wall of a body cavity such that the anchor member defines an opening; and
    inserting a device through the opening in the anchor member to anchor a distal portion of the device to the wall of the body cavity;
    engaging a body organ disposed within the body cavity with a distal-most end of the device; and
    sliding the device relative to the anchor member to manipulate the body organ.

2. The method of claim 1, wherein the device comprises an endoscope.

3. The method of claim 1, wherein the device comprises an accessory channel slidably coupled to an endoscope.

4. The method of claim 1, wherein endoscopically implanting the anchor member comprises inserting the anchor member through an endoscope, and manipulating the anchor member to engage the internal wall of the body cavity.

5. The method of claim 4, wherein a grasping device disposed through the endoscope is used to manipulate the anchor member.

6. The method of claim 4, wherein the anchor member includes a first terminal end that is implanted at a first anchor site on the internal wall of the body cavity, and a second terminal end that is implanted at a second anchor site on the internal wall of the body cavity such that the anchor member extends between the first and second anchor sites and the opening is formed between the anchor member and the internal wall of the body cavity.

7. The method of claim 1, wherein the anchor member comprises a hoop defining the opening and having first and second tissue-penetrating legs extending therefrom for engaging the wall of the body cavity.

8. The method of claim 1, wherein the anchor member comprises an elongate rod having first and second tissue-penetrating legs located on opposed terminal ends thereof for engaging the wall of the body cavity.

9. The method of claim 1, wherein the anchor member comprises a suture having first and second tissue-engaging members coupled to opposed terminal ends thereof for engaging the internal wall of the body cavity.

10. The method of claim 9, wherein the opening is formed between the suture and the internal wall of the body cavity when the first and second tissue-engaging members are implanted in the internal wall of the body cavity.

11. The method of claim 9, wherein the first and second tissue-engaging members are passed through the internal wall of the body cavity to the external surface of the body, the method further comprising manipulating the first and second tissue-engaging members to pull the device against the internal wall of the body cavity.

12. The method of claim 1, further comprising:
grasping a body part with a distal end of the device; and
sliding the device relative to the anchor member to manipulate the body part.

13. The method of claim 12, wherein sliding the device comprises applying tension to a proximal end of the device.

14. A surgical method, comprising:
inserting an anchor member endoscopically through a natural orifice;
implanting the anchor member directly in an internal wall of a body cavity;
advancing an endoscopic device through a natural orifice and inserting a distal end of the device through a hoop on the anchor member such that the endoscopic device is suspended in the body cavity by the anchor member;
engaging a body organ disposed within the body cavity with a distal-most end of the endoscopic device; and
sliding the endoscopic device relative to the hoop on the anchor member to reposition the body organ within the body cavity.

* * * * *